(12) United States Patent
Reetz et al.

(10) Patent No.: US 9,061,963 B2
(45) Date of Patent: Jun. 23, 2015

(54) PROCESS FOR PREPARING AROMATIC AND HETEROAROMATIC AMINES

(75) Inventors: Manfred Reetz, Marburg (DE); Gerlinde Mehler, Mülheim an der Ruhr (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/111,217

(22) PCT Filed: Apr. 3, 2012

(86) PCT No.: PCT/DE2012/100089
§ 371 (c)(1),
(2), (4) Date: Oct. 11, 2013

(87) PCT Pub. No.: WO2012/139561
PCT Pub. Date: Oct. 18, 2012

(65) Prior Publication Data
US 2014/0213785 A1  Jul. 31, 2014

(30) Foreign Application Priority Data
Apr. 14, 2011 (DE) .......... 10 2011 017 027

(51) Int. Cl.
| | | |
|---|---|---|
| C07D 215/38 | (2006.01) |
| C07D 217/22 | (2006.01) |
| C07D 295/033 | (2006.01) |
| C07D 213/74 | (2006.01) |
| C07C 209/10 | (2006.01) |
| C07B 43/04 | (2006.01) |

(52) U.S. Cl.
CPC .............. *C07C 209/10* (2013.01); *C07B 43/04* (2013.01); *C07D 213/74* (2013.01); *C07D 215/38* (2013.01); *C07D 217/22* (2013.01); *C07D 295/033* (2013.01)

(58) Field of Classification Search
USPC .......................................... 564/373, 374, 404
See application file for complete search history.

(56) References Cited

U.S. PATENT DOCUMENTS
| | | | |
|---|---|---|---|
| 6,124,462 A | 9/2000 | Li |
| 7,563,932 B2 | 7/2009 | Coggan et al. |
| 2004/0147392 A1 | 7/2004 | Li |

FOREIGN PATENT DOCUMENTS
| | | | |
|---|---|---|---|
| WO | 2006 074315 A2 | 7/2006 |

OTHER PUBLICATIONS

English translation of International Preliminary Report on Patentability issued by the International Bureau of WIPO Oct. 15, 2013.
Rataboul, et al; "New Ligands for a General Palladium-Catalyzd Amination of Aryl and Heteroaryl Chlorides"; Chem. Eur. J. 2004, 10, 2983-2990.
Bo et al; "Synthesis of Low-Generation, Aryl-/Alkyl-Type, Nonpolar Dendrons Carrying Protected Hydroxyalkyl Groups in the Periphery"; J. Org. Chem. 2002, 67, 5327-5332.
Wolfe et al; "Rational Development of Practical Catalysts for Aromatic Carbon-Nitrogen Bond Formation"; Acc. Chem. Res. 1998, 31, 805-818.
Surry et al; "Biaryl Phosphane Ligands in Palladium-Catalyzed Amination"; Angew. Chem. Int. Ed. 2008, 47, 6338-6361.
Hamann et al; "Sterically Hindered Chelating Alkyl Phosphines Provide Large Rate Accelerations in Palladium-Catalyzed Amination of Aryl iodides, Bromides, and Chlorides, and the First Amination of Aryl Tosylates"; J. Am. Chem. Soc. 1998, 120, 7369-7370.
Shen et al; "Palladium-Catalyzed Coupling of Ammonia and Lithium Amide with Aryl Halides"; J. Am. Chem. Soc. 2006, 128, 10028-10029.
Li, et al; "The First Phosphine Oxide Ligand Precursors for Transition Metal Catalyzed Cross-Coupling Reactions: C-C, C-N, and C-S Bond Formation on Unactivated Aryl Chlorides"; Angew. Chem. Int. Ed. 2001, 40, No. 8, 1513-1516.
Littke et al; "Palladium-Catalyzed Coupling Reactions of Aryl Chlorides"; Angew. Chem. Int. Ed. 2002, 41, 4176-4211.
Schlummer et al; "Palladium-Catalyzed C-N and C-O Coupling -A Practical Guide from an Industrial Vantage Point"; Adv. Synth. Catal. 2004, 346, 1599-1626.
Shen et al; "Highly Reactive, General and Lin-Lived Catalysts for Palladium-Catalyzed Amination of Heteroaryl and Aryl Chlorides, Bromides, and Iodides: Scope and Structure-Activity Relationships"; J. Am. Chem. Soc. 2008, 130, 6586-6596.
Singer, et al; "Development of nonproprietary phosphine ligands for the Pd-catalyzed amination reaction"; Tetrahedron Letters 47 (2006), 3727-3731.
Urgaonkar et al; "Application of a New Bicyclic Triaminophosphine Ligand in Pd-Catalyzed Buchwald-Hartwig Amination Reactions of Aryl Chlorides, Bromides, and Iodides"; J. Org. Chem. 2003, 68, 8416-8423.
International Search report for PCT/DE2012/100089 mailed Aug. 3, 2012.
Ackermann et al; "A Diaminochlorophosphine for Palladium-Catalyzed Arylations of Amines and Ketones"; Angew Chem. Int. Ed. 2006, vol. 45, pp. 7627-7630.
Ahmadibeni et al; "Solid-Phase Synthesis of Symmetrical 5', 5'-Dinucleoside Mono-, Di-, Tri-, and Tetraphosphodiesters"; Organic Letters; 2007, vol. 9, No. 22, pp. 4483-4486.
Kitas, et al; "Alternative Strategies for the Fmoc Solid-Phase Synthesis of O4-Phospho-L-tyrosine-Contaiing Peptides"; Helvetica Chemica Acta, vol. 74, 1991, pp. 1314-1328.

*Primary Examiner* — Shawquia Jackson
(74) *Attorney, Agent, or Firm* — Norris McLaughlin & Marcus, P.A.

(57) ABSTRACT

A process is described for preparing aromatic and heteroaromatic amines of the general formula (I) Ar—NR$^1$R$^2$, in which an aromatic compound with the general formula (II) Ar—X is reacted in the presence of a catalyst with an amine of the general formula (III) H—NR$^1$R$^2$ and a base, wherein the catalyst is selected from transition metal complexes having one or more ligands with the general formula (IV).

6 Claims, No Drawings

PROCESS FOR PREPARING AROMATIC AND HETEROAROMATIC AMINES

This application is a 371 of International Patent Application No. PCT/DE2012/100089, filed Apr. 3, 2012, which claims foreign priority benefit under 35 U.S.C. §119 of German Patent Application No. 10 2011 017 027.8, filed Apr. 14, 2011, the disclosures of which are incorporated herein by reference.

The present invention relates to a process for preparing aromatic and heteroaromatic amines from the corresponding aryl and heteroaryl halides or sulfonates in the presence of a catalyst and a base.

Aromatic and heteroaromatic amines are of great industrial interest. The preparation of these compounds by catalytic amination of the corresponding chlorine, bromine or iodine compounds to form arylamines is a conversion important in organic synthesis (B. Schlummer, U. Scholz, *Adv. Synth. Catal.* 2004, 346, 1599). In general, the reaction requires both a base for binding the liberated acid HX (X=Cl, Br or I) and a transition metal catalyst. Palladium, nickel, iron and cobalt are among the transition metals used. It has been found that palladium (Pd) is the most effective transition metal. In addition, ligands are necessary for stabilizing and activating the metal which in the oxidation state zero (Pd⁰) initiates the reaction by reductive insertion into the carbon-halogen bond. Unfortunately, it has been found that readily available and cheap phosphanes such as triphenylphosphane are not well-suited since their use leads to low or unusable yields. Breakthroughs in this field of research have been, in particular, the discoveries by Buchwald (*Acc. Chem. Res.* 1998, 31, 805; *J. Org. Chem.* 2000, 65, 5327; WO 2006/074315 A2; more recent review: *Angew. Chem. Int. Ed.* 2008, 47, 6338), by Hartwig (*J. Am. Chem. Soc.* 1998, 120, 7369; *J. Am. Chem. Soc.* 2006, 128, 10028; *J. Am. Chem. Soc.* 2008, 130, 6586) and by other authors (summary: A. F. Littke and G. C. Fu, *Angew. Chem. Int. Ed.* 2002, 41, 4176). According to these references, Pd complexes of bulky phosphanes, e.g. 1-8, catalyze the Pd-promoted amination the best since yields of more than 80% can be achieved for many aryl halides and different amine starting compounds.

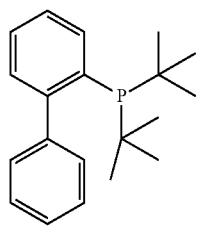

1

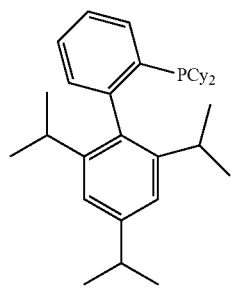

2

Cy = cyhclohexyl

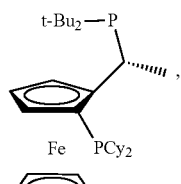

3

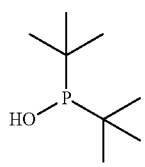

4

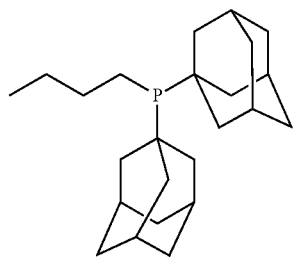

5

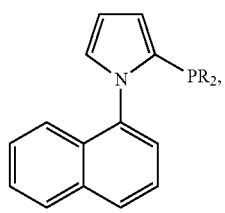

6

R = Cy
R = t-Bu

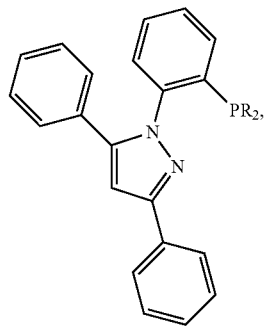

7

R = i-Pr
R = t-Bu

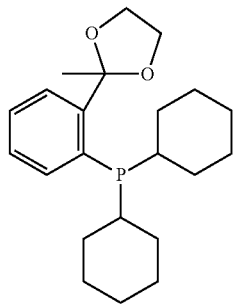

8

The obvious disadvantage of the above methods, which count as "state of the art", is the fact that bulky ligands of the above type are not readily available but instead their syntheses require not only expensive organolithium or organomagnesium reagents but also a plurality of stages under protective gas conditions and at low temperatures. Cyclic phosphorus compounds of the type 9-11 have likewise been used as ligands in Pd-catalyzed aminations of aryl halides, but the synthesis of the corresponding bulky diamines likewise requires a complicated multistage reaction sequence (L. Ackermann, et al, *Angew. Chem. Int. Ed.* 2006, 45, 7627; J. C. Verkade, et al, *J. Org. Chem.* 2003, 68, 8416). Although further bulky P ligands are also suitable for Pd-catalyzed aminations, they again require complicated syntheses (G. Y. Li, *Angew. Chem. Int. Ed.* 2001, 40, 1513; US Patent 20040147392, 2004; B. Schlummer, U. Scholz, *Adv. Synth. Catal.* 2004, 346, 1599; M. Beller, et al, *Chem. Eur. J.* 2004, 10, 2983; J. A. Coggan, et al, U.S. Pat. No. 7,563,932, 2009; R. A. Singer, et al, *Tetrahedron Lett.* 2006, 47, 3727).

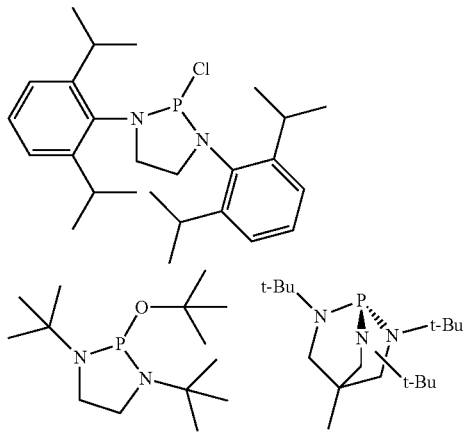

The processes known from the prior art require expensive phosphorus compounds which can be obtained only via complicated syntheses for preparing the aromatic amines. It was therefore an object of the present invention to provide a process in which aromatic and heteroaromatic amine compounds can be prepared in a simple way using inexpensive catalysts.

The present invention accordingly provides a process for preparing aromatic and heteroaromatic amines of the general formula I

$$Ar-NR^1R^2 \quad (I)$$

where

Ar is a substituted or unsubstituted aryl, heteroaryl, arylalkyl, heteroarylalkyl radical, $R^1$ and $R^2$ can be identical or different and are each H, a hydrocarbon group, for example a saturated or unsaturated, branched or linear alkyl group, alkenyl group, alkynyl group, aryl group, which may have suitable substituents, including heteroatom substituents, a heteroatom-containing hydrocarbon group which may have suitable substituents, and the radicals $R^1$ and $R^2$ may form a ring which can be 4- to 20-membered, saturated or unsaturated, alicyclic or heteroalicyclic and may have suitable substituents, in which an aromatic compound having the general formula II

$$Ar-X \quad (II)$$

where

Ar is as defined above and

X is F, Cl, Br, I or $OSO_2R^3$ in which $R^3$ is a hydrocarbon group, for example a saturated or unsaturated, branched or linear alkyl group, alkenyl group, alkynyl group, aryl group, which may have suitable substituents, including heteroatom substituents, is reacted in the presence of a catalyst with an amine of the general formula III

$$H-NR^1R^2 \quad (III)$$

where $R^1$ and $R^2$ are as defined above, and a base, characterized in that the catalyst is selected from among transition metal complexes which have one or more ligands having the general formula IV

where $R^3$, $R^4$, $R^5$ and $R^6$ can be identical or different and are each H, a linear or branched $C_1$-$C_6$-alkyl radical which may optionally be substituted or $R^3$ and $R^4$ and/or $R^5$ and $R^6$ are joined to one another to form a ring, Y is halogen or an —$OR^7$ radical, where $R^7$ is H or a linear or branched $C_1$-$C_6$-alkyl chain which may optionally be substituted or an aryl radical which may optionally be substituted.

The phosphorus compounds having the general formula IV which are used according to the invention are compounds which can be prepared in a simple way from inexpensive starting materials. It is possible to prepare aromatic and heteroaromatic amines inexpensively using these catalysts.

The catalysts used according to the invention are transition metal complexes which have one or more ligands having the general formula IV.

The ligands having the formula IV are derivatives of phosphorous acid. The radicals $R^3$, $R^4$, $R^5$ and $R^6$ can be identical or different and are preferably selected from among linear or branched alkyl and alkenyl groups having from 1 to 6 carbon atoms. $R^3$, $R^4$, $R^5$ and $R^6$ are preferably an isopropyl, isobutyl, tert-butyl, neopentyl and/or tert-amyl radical, with isopropyl and tert-butyl being particularly preferred. In a particularly preferred embodiment, $R^3$ and $R^5$ and/or $R^4$ and $R^6$ are i-propyl or tert-butyl.

The radical Y is halogen, in particular Cl, Br or I, or an —$OR^7$ radical, where $R^7$ is H, a linear or branched $C_1$-$C_6$-alkyl chain which may optionally be substituted or an aryl radical which may optionally be substituted. Y is preferably selected from among Cl, Br and —$OR^7$, where $R^7$ is preferably i-propyl or tert-butyl.

The term hydrocarbon group used in the context of the invention is a saturated or unsaturated, branched or linear alkyl group, alkenyl group, alkynyl group, aryl group, which may have suitable substituents, including heteroatom substituents, or a heteroatom-containing hydrocarbon group.

Alkyl can be unbranched (linear) or branched and has from 1 to 6 carbon atoms. Alkyl is preferably methyl, ethyl, propyl, isopropyl, butyl, isobutyl, sec-butyl or tert-butyl, likewise pentyl, 1-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Alkyl can also be a halogenated alkyl radical, e.g. trifluoromethyl, pentafluoroethyl or 1,1,1-trifluoroethyl.

Cycloalkyl is preferably cyclopropyl, cyclobutyl, cyclopentyl, cyclohexyl or cycloheptyl. Alkylene is preferably methylene, ethylene, propylene, butylene, pentylene or hexylene, or else branched alkylene.

Alkenyl is preferably vinyl.

Alkynyl is preferably C≡CH.

Halogen is F, Cl, Br or I.

Alkoxy is preferably methoxy, ethoxy, propoxy or butoxy.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3- or -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-isoquinolyl, 1,2,3,4-tetrahydro-1-, -2-, -3-, -4-, -5-, -6-, -7- or -8-quinolyl, 2-, 3-,-5-, 6-, 7- or 8-3,4-dihydro-2H-benzo-1,4-oxazinyl.

Optionally substituted means unsubstituted or mono-substituted, disubstituted, trisubstituted, tetrasubstituted or pentasubstituted.

Aryl is preferably phenyl, naphthyl or biphenyl.

Arylalkyl is preferably benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

Examples of substituents are $C_1$-$C_4$-alk(en)yl, aryl, heteroaryl, halogen such as F, Cl, Br, I, $NO_2$, $NR^8R^9$, where $R^8$ and $R^9$ can be identical or different and are each H or a $C_1$-$C_6$-alkyl group, etc.

Possible precursors for the transition metal complexes are, in particular, compounds of the iron metals, for example the salts of iron, palladium, nickel, cobalt, platinum, rhodium or ruthenium. It is also possible to use compounds in which the transition metal is in the oxidation state zero. Particularly preferred transition metals are palladium and iron. Particularly suitable precursors are Pd salts such as $Pd(OAc)_2$ (Ac=acetyl), $Pd(acac)_2$ (acac=acetylacetonate), $(allPdCl)_2$ (all=allyl) or $PdCl_2$, preferably $Pd(OAc)_2$ or $PdCl_2$, also $Pd^0$ complexes such as $Pd_2(dba)_3$ and $Pd(dba)_2$ (dba=dibenzylideneacetone). In the case of iron, salts of the type $FeCl_2$ or $FeCl_3$ deserve particular mention.

To carry out the process of the invention, the amount of transition metal used can vary in the range from 0.01 to 15 mol %, with the molar ratio of ligand to transition metal being able to be set in the range from 3:1 to 1:1, preferably about 2:1.

According to the invention, the process is carried out in the presence of a base. Suitable bases are, in particular, alkali metal alkoxides, alkali metal hydroxides, alkali metal carbonates and alkali metal phosphates, ammonia and also organic bases. For example, it is possible to use lithium, sodium, potassium or cesium alkoxides (ROmetal), where R can be a primary, secondary or tertiary $C_1$-$C_4$-alkyl radical, in particular $CH_3ONa$, $(CH_3)_3CONa$, $(CH_3)_3COK$, $(CH_3)_2(C_2H_5)$CONa or $(CH_3)_2(C_2H_5)COK$, preferably tertiary alkoxides. LHMDS ($Li(NSiMe_3)_2$), NaOH, KOH, $(n-C_4H_9)_4NOH$, $Na_2CO_3$, $K_2CO_3$, $Cs_2CO_3$ and $K_3PO_4$ can also serve as base. Examples of organic bases are $C_1$-$C_6$-alkylamine, di($C_2$-$C_6$-alkyl)amine, benzylamine, piperidine and/or morpholine. Any mixtures of the above bases can also be used.

The reaction can be carried out in conventional polar or nonpolar organic and also ionic solvents, for example toluene, THF, dimethoxyethane (DME), dimethyl-formamide (DMF), dimethyl sulfoxide (DMSO), N-methyl-2-pyrrolidone (NMP) or 1,4-dioxane and any mixtures thereof. The reaction can also be carried out in aqueous solutions. It is also possible to use the amine component itself as solvent. This is possible, for example, when ammonia, $C_1$-$C_6$-alkylamine, di($C_2$-$C_6$-alkyl)-amine, benzylamine, piperidine, morpholine or any mixtures thereof is/are used as amine component.

The reaction can be carried out at from room temperature up to a temperature of 180° C., preferably from 70° C. to 120° C.

EXAMPLES

Example 1

Amination of Substituted Aryl Halides by Means of Morpholine in the Presence of (i-$Pr_2N$)$_2$P—R Ligands Typical examples of the process of the invention are the reactions of aryl chlorides and aryl bromides with morpholine (see scheme below):

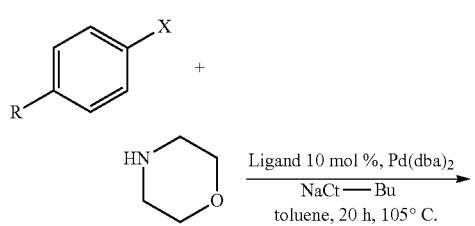

-continued

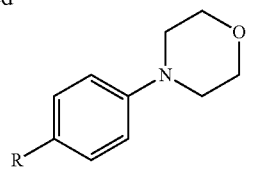

To carry out the process, aryl halide (25 mmol) and 3.13 g of morpholine (30 mmol) (2.62 ml) were made up to 25 ml with toluene.

29 mg of Pd(dba)$_2$ (0.05 mmol) and 125 mg of Na—Ot-Bu (1.30 mmol) were weighed into the reaction vessel. A solution of 0.1 mmol of ([(CH$_3$)$_2$CH]$_2$N)$_2$POC(CH$_3$)$_3$ in 2 ml of toluene was pipetted into the Pd(dba)$_2$ solution and stirred for 10 minutes. 1 ml of substrate solution (1.0 mmol of aryl halide, 1.2 mmol of morpholine) was subsequently pipetted in and the mixture obtained was stirred at 105° C. for 20 hours.

After the reaction was complete, the reaction mixture was allowed to cool to room temperature and 50 ml of diethyl ether and 50 ml of saturated NaCl solution were added. The aqueous phase was washed twice with 50 ml of diethyl ether, dried over MgSO$_4$ and the solvent was removed by means of a rotary evaporator. The reaction product was isolated from the residue by means of column chromatography (silica gel 60, L=11 cm, 0=1.5 cm, pentane/ether=4:1).

As an alternative, 2.5 g of silica gel 60 and 15 ml of diethyl ether were added to the reaction mixture after cooling to room temperature, the mixture was stirred for 10 minutes, silica gel was filtered off on a fluted filter, washed with plenty of ether, the diethyl ether was removed by means of a rotary evaporator and the residue was dried under reduced pressure.

The purity of the products obtained was determined by means of gas chromatography. The results are shown in table 1.

TABLE 1

| | R—⌬—X | (i-Pr$_2$N)$_2$PCl Yield (%) | (i-Pr$_2$N)$_2$POt-Bu Yield (%) | (i-Pr$_2$N)$_2$POH Yield (%) |
|---|---|---|---|---|
| 1 | R = H, X = Br | 74.8 | 100 | 43.9 |
| 2 | R = H; X = Cl | 92.2 | 86.0 | — |
| 3 | R = CN; X = Br | 31.3 | 47.5 | — |
| 4 | R = NO$_2$; X = Br | 36.8 | 71.0 | — |
| 5 | R = Me; X = Br | 84.0 | 88.0 | 53.3 |
| 6 | R = OMe; X = Br | 93.0 | 100 (s.u.) | — |
| 7 | R = Ph; X = Br | 72.7 | 76.3 | 45.2 |
| 8 | (1-bromonaphthalene) | 75.4 | 85.2 | 31.6 |
| 9 | R = Me; X = Cl | — | 92.4 | |
| 10 | R = t-Bu; X = Br | — | 92.9 | |
| 11 | R = t-Bu; X = Cl | — | 94.6 | |
| 12 | R = F; X = Br | — | 90.3 | |
| 13 | R = Ph; X = Cl | — | 92.8 | |
| 14 | (2-bromonaphthalene) | — | 93.6 | |

S/C = 20; Pd/P = 1:1

Example 2

Amination of Aryl Halides by Means of Piperidine and N-methylbenzylamine in the Presence of (i-Pr$_2$N)$_2$P—R Ligands

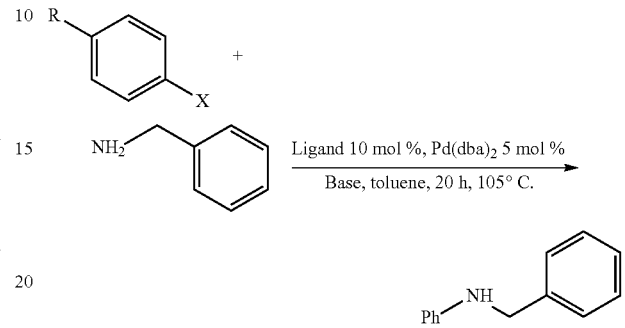

TABLE 2

S/C = 20; Pd/P = 1:2

| | Ligand | Amine/ArX | Yield (%) Product |
|---|---|---|---|
| 1 | (i-Pr$_2$N)$_2$PCl | Piperidine/PhBr | 84.6 |
| 2 | (i-Pr$_2$N)$_2$POt-Bu | Piperidine/PhBr | 73.9 |
| 3 | (i-Pr$_2$N)$_2$PCl | Piperidine/PhCl | 90.2 |
| 4 | (i-Pr$_2$N)$_2$POt-Bu | Piperidine/PhCl | 79.9 |
| 5 | (i-Pr$_2$N)$_2$PCl | Me(H)NBn/PhBr | 83.6 |
| 6 | (i-Pr$_2$N)$_2$POt-Bu | Me(H)NBn/PhBr | 83.3 |
| 7 | (i-Pr$_2$N)$_2$PCl | Me(H)NBn/PhCl | 78.8 |
| 8 | (i-Pr$_2$N)$_2$POt-Bu | Me(H)NBn/PhCl | 77.8 |

Example 3

Amination of Aryl Halides by Means of Benzylamine in the Presence of (i-Pr$_2$N)$_2$P—Ot-Bu ligand

TABLE 3

| | R—⌬—X | (i-Pr$_2$N)$_2$POt-Bu Yield (%) |
|---|---|---|
| 1 | R = H; X = Br | 74.4 |
| 2 | R = H; X = Cl | 70.0 |
| 3 | R = CN; X = Cl | 51.4 |
| 4 | R = Me; X = Br | 70.0 |
| 5 | R = OMe; X = Br | 58.7 |
| 6 | R = Ph; X = Br | 88.4 |
| 7 | (1-bromonaphthalene) | 90.0 |

S/C = 20; Pd/P = 1:2

Example 4

Amination of Aryl Bromide by Means of Morpholine in the Presence of Various Phosphorus Ligands

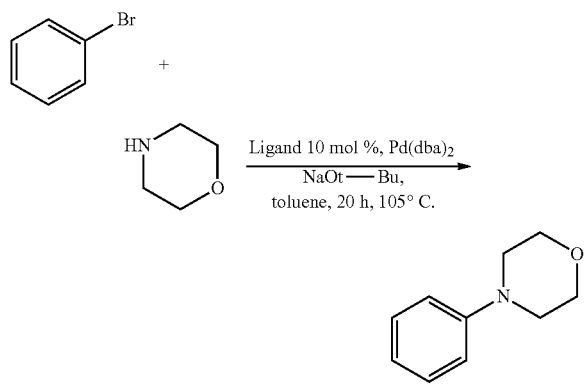

TABLE 4

S/C = 20; Pd/P = 1:2

| | | Yield (%) |
|---|---|---|
| | Ligand = (i-Pr$_2$N)$_2$P—R | |
| 1 | R = —Cl | 74.8 |
| 2 | R = —OH | 87.2 |
| 3 | R = —Ot-Bu | 100 |
| 4 | R = —O-adamantyl | 86.0 |
| 5 | R = -Benzyl | 86.7 |
| 6 | R = —NMe$_2$ | 82.8 |
| | Ligand = (Ot-Bu)$_2$P—NR$_2$ | |
| 7 | R = —Et | 88.2 |
| 8 | R = -i-Pr | 89.3 |

Example 5

Amination of Bromoheteroarenes by Means of Morpholine in the Presence of (i-Pr$_2$N)$_2$P—Ot-Bu Ligand

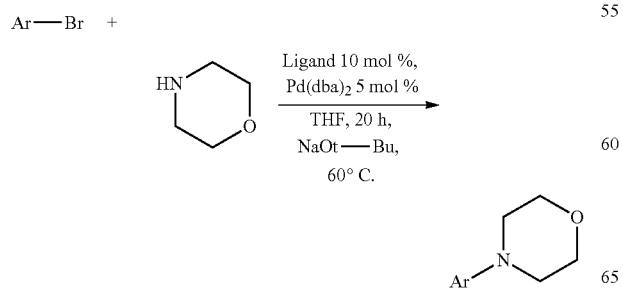

TABLE 5

| | Ar—Br | Yield (%) |
|---|---|---|
| 1 |  | 96.6 |
| 2 |  | 99.9 |
| 3 |  | 99.9 |

S/C = 20; Pd/P = 1:2

The invention claimed is:
1. A process for preparing aromatic amines of formula (I):

Ar—NR$^1$R$^2$ (I)

where
Ar is a substituted or unsubstituted aryl, heteroaryl, arylalkyl, heteroarylalkyl radical,
R$^1$ and R$^2$ can be identical or different and are each H, a hydrocarbon group, a heteroatom-containing hydrocarbon group which may have suitable substituents, and the radicals R$^1$ and R$^2$ may form a ring which can be 4- to 20-membered, saturated or unsaturated, alicyclic or heteroalicyclic and may have suitable substituents,
said process comprising reacting an aromatic compound having formula II:

Ar—X (II)

where
Ar is as defined above and
X is F, Cl, Br, I or OSO$_2$R$^3$ in which R$^3$ is a hydrocarbon group,
in the presence of a catalyst with an amine of formula III:

H—NR$^1$R$^2$ (III)

where R$^1$ and R$^2$ are as defined above,
and a base,
wherein the catalyst is selected from among transition metal complexes which have one or more ligands having formula IV:

(IV)

where
R$^3$, R$^4$, R$^5$ and R$^6$ can be identical or different and are each H, a linear or branched C$_1$-C$_6$-alkyl radical which may optionally be substituted or R$^3$ and R$^4$ and/or R$^5$ and R$^6$ are joined to one another to form a ring, Y is halogen or an —OR$^7$ radical, where R$^7$ is H or a linear or branched $C_1$-$C_6$-alkyl chain which may optionally be substituted or an aryl radical which may optionally be substituted.

2. The process as claimed in claim 1, wherein Y is Cl, Br or —OR$^7$, where R$^7$ is i-propyl or tert-butyl.

3. The process as claimed in claim 1, wherein R$^3$ and R$^5$ and/or R$^4$ and R$^6$ are i-propyl or tert-butyl.

4. The process as claimed in claim 1, wherein the base is selected from among alkali metal hydroxides, alkali metal alkoxides, alkali metal carbonates, alkali metal phosphates, ammonia, $C_1$-$C_6$-alkylamine, di($C_1$-$C_6$-alkyl)amine, benzylamine, piperidine and morpholine.

5. The process as claimed in claim 1, wherein the transition metal is selected from among iron, palladium, nickel, cobalt, platinum, rhodium and ruthenium.

6. The process as claimed in claim 5, wherein the transition metal complex is prepared from transition metal compounds selected from among $Pd(OAc)_2$, $Pd(acac)_2$, $(allPdCl)_2$, $PdCl_2$, $Pd_2(dba)_3$ and $Pd(dba)_2$.

* * * * *